United States Patent [19]

Sebestyén et al.

[11] Patent Number: 4,868,172
[45] Date of Patent: Sep. 19, 1989

[54] PHARMACEUTICAL COMPOSITION COMPRISING AN ORGANIC ZINC COMPLEX AND A PROCESS FOR PREPARING THE ACTIVE SUBSTANCE

[75] Inventors: Gyula Sebestyén; István Simonyi; Gizella Miholics; Márta Kovács; Frigyes Görgényi; Márton Fekete; Pál Vágó; István Seres; Egri János; Mária Szeli, all of Budapest, Hungary

[73] Assignee: BASF Aktiengesellschaft, Ludwigshafen, Fed. Rep. of Germany

[21] Appl. No.: 38,656

[22] Filed: Apr. 15, 1987

[30] Foreign Application Priority Data

Apr. 18, 1986 [HU] Hungary ............................... 1623/86

[51] Int. Cl.$^4$ ..................... A61K 31/555; A61K 9/12
[52] U.S. Cl. ........................................ 514/187; 424/43
[58] Field of Search ........................... 514/187; 421/43

[56] References Cited

PUBLICATIONS

Chemical Abstracts 83: 157288m (1975).
Chemical Abstracts 88: 108h (1978).

Primary Examiner—Jerome D. Goldberg
Attorney, Agent, or Firm—Keil & Weinkauf

[57] ABSTRACT

The invention refers to a novel pharmaceutical composition having especially antimycotic activity and comprising the zinc complex of 5-chloro-7-iodo-8-hydroxyquinoline of formula (I)

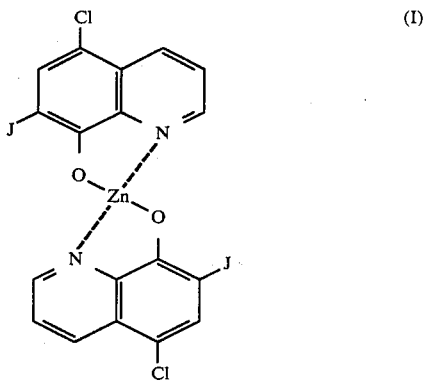

and one or more pharmaceutically acceptable carriers.

The pharmaceutical composition of the invention can be used for the effective treatment of mycotic infections on the skin surface, mucous membranes or nails.

The complex of formula (I) is prepared by reacting a solution of an alkali metal salt of 5-chloro-7-iodo-8-hydroxyquinoline with a solution containing an excess of an inorganic or organic zinc salt or a zinc complex having a lower stability constant than that of the complex of formula (I) and separating the product precipitated.

11 Claims, No Drawings

PHARMACEUTICAL COMPOSITION COMPRISING AN ORGANIC ZINC COMPLEX AND A PROCESS FOR PREPARING THE ACTIVE SUBSTANCE

The invention refers to a novel pharmaceutical composition having especially atimycotic activity and to a process for preparing the active substance being the zinc complex of 5-chloro-7-iodo-8-hydroxyquinoline of formula (I)

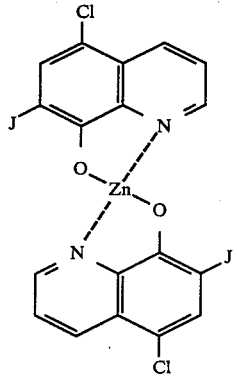

5-Chloro-7-iodo-8-hydroxyquinoline is known to have antibacterial activity, thus, it is employed for the treatment of amoebic colities (A. Burger, Medicinal Chemistry, 1, p. 540, Wiley-Interscience, New York, 1970).

The zinc chelate of 5-chloro-7-iodo-8-hydroxyquinoline of the formula (I) was used for analytical determinations (Acta Pharm. Hung., 32, 246). Also the solubility of the complex of formula (I) was investigated (Chem. Abstr., 50, 652d) and the determination of the complex by mass spectrometry was described [Chem. Abstr., 83, 157288m (1975)].

5-Chloro-7-iodo-8-hydroxyquinoline labelled with $^{14}C$ was reacted with $^{65}Zn$ ions to give the corresponding labelled chelate that was used for the treatment of rabbits, and the concentration of the chelate in the tibial nerve was determined [Chem. Abstr., 88, 108h (1978)].

In summary, it can be established that in the prior art these is not indication of a therapeutically valuable biological activity of the complex of the formula (I), furthermore, an economical process for preparation the complex is not known, either.

Now it has been found that the complex of formula (I) has an extremely high antimycotic activity as shown by the following in vitro tests.

The antimycotic activity of the complex of formula (I) was compared with that of 5-chloro-7-iodo-8-hydroxyquinoline on the following fungus strains:
Trichlophyton mentagrophyte (A)
Microsporum canis (B)
Candida albicans (C)
Aspergillus niger (D)

The test were performed according to the prescriptions of the United States' Pharmacopoeia XXI on an ointment comprising 0.04 per cent of the complex of formula (I) and 0.036 per cent of 5-chloro-7-iodo-8-hydroxyquinoline, respectively. Ointment samples prepared aseptically and weighing 50 g were artifically infected with the cells and spores, respectively, of the microorganisms listed above to obtain a starting germ count of about $5 \times 10^5/g$. Aliquots of 1 g were removed from the samples directly after the infection (time 0), then after 1, 2, 3, 4, 5, 6 and 7 days, and the germ count was determined in each case by means of the plate pouring method. Three parallel tests were performed with both compounds and the four strains of fungi. The average values of the results obtained are given in Table 1.

TABLE 1

| | | In vitro antimycotic activity | | | | | | | |
|---|---|---|---|---|---|---|---|---|---|
| | | Germ count | | | | | | | |
| Microorganism | Compound | 0 hour | 1 day | 2 days | 3 days | 4 days | 5 days | 6 days | 7 days |
| | | | | | after infection | | | | |
| A | Zinc complex of 5-chloro 7-iodo-8-hydroxyquinoline | $6.65 \times 10^5$ | $8.1 \times 10^4$ | 0 | 0 | 0 | 0 | 0 | 0 |
| | 5-Chloro-7-iodo-8-hydroxyquinoline | $6.55 \times 10^5$ | $4.1 \times 10^4$ | $3.5 \times 10^4$ | $2.5 \times 10^3$ | $2.5 \times 10^3$ | $2.8 \times 10^2$ | 0 | 0 |
| B | Zinc complex of 5-chloro-7-iodo-8-hydroxyquinoline | $4.2 \times 10^5$ | $1.1 \times 10^5$ | $2 \times 10^4$ | $1.4 \times 10^2$ | 0 | 0 | 0 | 0 |
| | 5-Chloro-7-iodo-8-hydroxyquinoline | $3.8 \times 10^5$ | $3.1 \times 10^4$ | $3.15 \times 10^4$ | $2.6 \times 10^3$ | $1.2 \times 10^3$ | $10^2$ | 10 | 0 |
| C | Zinc complex of 5-chloro-7-iodo-8-hydroxyquinoline | $6.1 \times 10^5$ | $2.1 \times 10^3$ | $1.8 \times 10^2$ | 0 | 0 | 0 | 0 | 0 |
| | 5-Chloro-7-iodo-8-hydroxyquinoline | $6.22 \times 10^5$ | $4.2 \times 10^5$ | $3.8 \times 10^4$ | $2.1 \times 10^4$ | $5.4 \times 10^3$ | $5.2 \times 10^3$ | $5.5 \times 10^2$ | $4 \times 10$ |
| D | Zinc complex of 5-chloro-7-iodo-8-hydroxyquinoline | $5.5 \times 10^5$ | $3.2 \times 10^4$ | $1.35 \times 10^2$ | 0 | 0 | 0 | 0 | 0 |
| | 5-Chloro-7-iodo-8-hydroxyquinoline | $5.4 \times 10^5$ | $4.1 \times 10^5$ | $4.0 \times 10^4$ | $3.1 \times 10^3$ | $1.4 \times 10^2$ | $2 \times 10$ | 0 | 0 |

From Table 1 it can be seen that the germ count is lowered to zero by the zinc complex of 5-chloro-7-iodo-8-hydroxyquinoline in a much shorter time than by the 5-chloro-7-iodo-8-hydroxyquinoline in case of each microorganism tested. Thus, the samples comprising the zinc complex of formula (I) and infected with the strain Trichlophyton mentagrophytes become free from germs already on day 2, while the samples containing 5-chloro-7-iodo-8-hydroxyquinoline need 6 days to become germ-free.

It is surprising for an expert that the complex of the formula (I) exerts a powerful antimycotic action in a much shorter time than the corresponding zinc-free compound, i.e. 5-chloro-7-iodo-8-hydroxyquinoline.

The dermal toxicity of the complex of formula (I) was determined on rats (CFY) weighing about 180 g at the beginning of the test. Each group consisted of 5 male and 5 female rats.

The animals were anaesthetized with ether and a dorsal skin surface measuring 5 cm by 5 cm was shaved, then covered with an ointment comprising 10 per cent of the compound of formula (I). The dosage was 10 g of ointment/1 kg of body weight.

The animals were exposed to the ointment for 24 hours, then observed for any signs of toxicity during 14 days. Neither toxic clinical symptoms, nor mortality were experienced. The hair growth of the treated rats was normal for these animal species.

Thus, the complex of formula (I) did not show any dermal toxicity in a dosage of 1 g/kg.

From the above test results it can be concluded that the zinc complex of 5-chloro-7-iodo-8-hydroxyquinoline of formula (I) can be used for the therapy of mycosis. In the therapy, the patient is treated with a therapeutically active amount of a compound of formula (I) or a pharmaceutical composition comprising it.

The pharmaceutical composition of the invention comprises the zinc complex of 5-chloro-7-iodo-8-hydroxyquinoline of formula (I) and one or more pharmaceutically acceptable carrier(s).

The pharmaceutical compositions of the invention can be solid or liquid. The solid pharmaceutical compositions may be powders, dusting powders, ointments, vaginal suppositories, capsules, tablets dragees etc. The liquid pharmaceutical compositions can be emulsions, suspensions, gels etc. The emulsions or suspensions of the invention can be converted to aerosols, too, by means of propellants.

The parmaceutical composition of the invention contains, in general, 0.1 to 90 percent of the complex of formula (I).

Preferred pharmaceutical compositions of the invention are ointments, vaginal suppositories and dusting powders being suitable in the first place for local treatment. For systemic treatment, preferred pharmaceutical compositions can be capsules, tablets or dragees.

The dialy dosage of the compound of the formula (I) is, in general, about 0.01 mg to 1 g depending on various factors such as the state and weight of the patient, dosage form etc.

The pharmaceutical composition of the invention comprises pharmaceutically acceptable carrier(s) in addition to the active substance (see e.g. Remington's Pharmaceutical Sciences, 16th Edition, Mack Publishing Company, Easton, USA, 1980).

Preferred carriers are: water; alkanols, for example monobasic alcohols such as isopropanol or cetyl-stearyl alcohol, dibasic alcohols such as poly(ethylene glycol), tribasic alcohols such as glycerol; fat-like substances, for example triglycerides of fatty acids; fatty acids or the metal salts thereof such as stearic acid, magnesium stearate or zinc stearate; liquid or solid hydrocarbons such as liquid paraffin or vaseline; silica or silicates such as bentonite or talc; metal oxids such as zinc oxide; alginic acid salts and esters thereof; poly(vinyl-pyrrolidone); polysaccharides such as starch; cellulosic derivatives such as cellulose ethers and cellulose esters; polymers such as polymethacrylates; surface active agents such as alkyl ethers of poly(ethylene glycol) or sorbitane esters of fatty acids; buffers and agents for pH control such as sodium acetate or triethanol amine; preservatives such as methyl p-hydroxybenzoate; etc.

The pharmaceutical compositions of the invention are prepared by mixing the complex of formula (I) with one or more suitable carrier(s) in a manner known per se.

The pharmaceutical compositions of the invention can be employed for the effective treatment of mycotic infections on the skin surface, mucous membranes or nails. For this purpose, the infected area is contacted with a therapeutically active amount of the complex of formula (I), or a therapeutically active amount of it is administered to the patient having mycotic infection.

The complex of formula (I) can be prepared from 5-chloro-7-iodo-8-hydroxyquinoline by essentially salt formation or from the corresponding zinc complex of 8-hydroxyquinoline by chlorination and iodination or from the corresponding zinc complex of 5-chloro-8-hdyroxyquinoline by iodination or from the corresponding zinc complex of 7-iodo-8-hydroxyquinoline by chlorination.

It is preferred to react a solution of an alkali metal salt - preferably sodium or potassium salt - of 5-chloro-7-iodo-8-hydroxyquinoline with a solution comprising an excess of an organic or inorganic zinc salt or a zinc complex having a lower stability constant than that of the compound of formula (I) and to separate the product precipitated.

In general, the zinc reactant is taken in excess as compared to the amount required by stoichiometry. Prferably, an excess of 10 to 30 percent is used.

For the complex formation, preferred zinc salts include zinc sulfate, zinc chloride, zinc acetate etc. The zinc complexes used as zinc reagent must have a lower stability than that of the compound of formula (I). Preferred zinc complexes include alkali tetrahydroxo zincate, zinc tetrammine hydroxide etc.

To prepare the solution of the alkali metal salt of 5-chloro-7-iodo-8-hydroxyquinoline as well as of the zinc reagent, solvents such as water, alkanols, e.g. methanol or ethanol, dimethyl formamide etc. or a mixture thereof are employed.

The alkali metal salt of 5-chloro-7-iodo-8-hydroxyquinoline is prepared from 5-chloro-7-iodo-8-hydroxyquinoline with an equimolar amount of an alkali metal hydroxide, then the solution of the zinc reagent is added to the solution of the alkali metal salt of 5-chloro-7-iodo-8-hydroxyquinoline. The suitable reaction medium dissolves the alkali metal salt of 5-chloro-7-iodo-8-hydroxyquinoline but practically does not dissolve the complex of formula (I). Preferred reaction media are mixtures of methanol and water. If necessary, the mother liquor of the compound of formula (I) can be, of course, concentrated by evaporation.

According to a preferred process of the invention, the complex of formula (I) can be prepared in a yield of about 85 percent. The purity of the product is suitable for pharmaceutical purposes.

The complex of formula (I) can be prepared also from a solution of 5-chloro-7-iodo-8-hydroxyquinoline by means of a cation exchange resin. In this case, zinc ions are bound to the cation exchange resin by treating the resin with a solution comprising zinc ions such as an aqueous zinc chloride solution, then the resin is eluted with a solution of 5-chloro-7-iodo-8-hydroxyquinoline in e.g. dimethyl formamide, and the eluate is concentrated.

Although the preparation of the zinc complexes of 8-hydroxyquinoline and halogenated 8-hydroxyquinolines is known, no teaching is available for the economical manufacture of the complex of formula (I).

The invention is further elucidated by means of the following Examples, without limiting the scope claimed.

EXAMPLE 1

The solution of 22.0 g (0.55 mole) of sodium hydroxide in 150 ml of water is quickly added to 163.0 g (0.53 mole) of 5-chloro-7-iodo-8-hydroxyquinoline suspended in 1500 ml of methanol at 30° C. The mixture is stirred and after 2 to 2.5 hours a dark green solution is obtained. To this solution comprising the sodium salt of 5-chloro-7-iodo-8-hydroxyquinoline in methanol, the solution of 95.0 g (0.33 mole) of zinc sulfate heptahydrate in 250 ml of water is added at room temperature. The yellow, compact solid formed is stirred for further 3 hours, then filtered and thoroughly washed with water. The product is dissolved in a mixture of 600 ml of dimethyl formamide and 50 ml of water under boiling, treated with 10 g of active carbon, filtered and the filtrate is stirred at 25° C. for 8 hours. The precipitate is filtered, suspended in 300 ml of methanol, the suspension obtained is stirred for 1 hour at the boiling point of then methanol, then cooled to room temperature. The product is filtered and dried to constant weight at 80° C.

In this way, 138.0 g of the zinc complex of 5-chloro-7-iodo-8-hydroxyquinoline are obtained. Yield: 82 percent. M.p.: 280° C. (under decomposition).

Analysis for $C_{18}H_8Cl_2I_2N_2O_2Zn$; calculated: C 32.05%, H 1.20%, N 4.15%, I 37.63%, Zn 9.69%; found: C 32.70%, H 1.30 5, N 4.04% I 37.03%, Zn 9.97%.

EXAMPLE 2

The procedure of Example 1 is repeated but the aqueous solution of zinc sulfate heptahydrate is replaced by the solution of 60.0 g (0.33 mole) of zinc chloride comprising 25 percent of crystal water in 250 ml of water. 145.5 g of the zinc complex of 5-chloro-7-iodo-8-hydroxyquinoline are obtained. Yield: 86.5 percent. M.p.: 280° C. (under decomposition).

EXAMPLE 3

The process of Example 1 is repeated but 72.4 g (0.33 mole) of zinc acetate dihydrate in 250 ml of water are used as the zinc reagent. Thus, 123.0 g of the zinc complex of 5-chloro-7-iodo-8-hydroxyquinoline are obtained. Yield: 73 percent. M.p.: 282° C. (under decomposition).

EXAMPLE 4

The procedure of Example 1 is repeated with the modification that a solution of sodium tetrahydroxo zincate [$Na_2Zn(OH)_4$] in water is used as the zinc reagent. Thus, 108.2 g of the zinc complex of 5-chloro-7-iodo-8-hydroxyquinoline are obtained. Yield: 64 percent. M.p.: 282° C. (under decomposition).

The solution of sodium tetrahydroxo zincate is prepared as follows: 93.7 g (0.33 mole) of zinc sulfate heptahydrate are dissolved in 125 ml of water, and the solution obtained is added to 28.0 g (0.7 mole) of sodium hydroxide in 125 ml of water. The solution thus obtained is reacted with the sodium salt of 5-chloro-7-iodo-8-hydroxyquinoline.

EXAMPLE 5

The procedure of Example 1 is repeated with the difference that an aqueous solution of zinc tetrammine hydroxide [$Zn(NH_3)_4(OH)_2$] is used as zinc reagent. Thus, 114.0 g of the zinc complex of 5-chloro-7-iodo-8-hydroxyquinoline are obtained. Yield: 67 percent. M.p.: 281° C. (under decomposition).

The solution of zinc tetramine hydroxide is prepared as follows: 100 ml of concentrated aqueous ammonia is poured to 93.7 g (0.33 mole) of zinc sulfate heptahydrate in 150 ml water, and the solution obtained is reacted with the sodium salt of 5-chloro-7-iodo-8-hydroxyquinoline.

EXAMPLE 6

| Ointment (of hydrophilic character) | |
| --- | --- |
| zinc complex of 5-chloro-7-iodo-8-hydroxyquinoline | 10 g |
| stearine | 2.7 g |
| paraffin oil | 12.6 g |
| cetyl-stearyl alcohol | 4.5 g |
| wax (cera alba) | 0.9 g |
| vaseline (white) | 4.5 g |
| Brij ® 58 [poly(ethyleneglycol) cetyl ether, degree of polymerisation: 20, manufacturer: Atlas] | 1.8 g |
| Span ® 60 (sorbitane monostearate, manufacturer: Atlas) | 2.25 g |
| methyl p-hydroxybenzoate | 0.18 g |
| distilled water to | 100 g |

The stearine, paraffin oil, cetyl-stearyl alcohol, vaseline and Span ® 60 are melted at about 80° C., stirred and filtered (lipophilic phase). The methyl p-hydroxybenzoate and Brij ® 58 are dissolved in the distilled water under boiling, the solution obtained is filtered and cooled to about 70° C. The warm aqueous solution is added to the lipopohilic phase of 65° C. in several portions under stirring. An emulsion of the type oil in water is obtained which is left to cool under stirring. Then, the zinc complex of 5-chloro-7-iodo-8-hydroxyquinoline is added in small portions under stirring and the composition is homogenized for 15 minutes. The homogeneous ointment is filled into tubes.

EXAMPLE 7

| Ointment (of lipophilic character) | |
| --- | --- |
| Zinc complex of 5-chloro-7-iodo-8-hydroxyquinoline | 8.0 g |
| vaseline (white) | 20.0 g |
| paraffin oil | 52.0 g |
| cholesterol | 1.4 g |
| Miglyol ® 812 (a mixture of triglycerides of saturated fatty acids of vegetable origin, manufacture: Dynamit-Nobel) | 2.5 g |
| Span ® 60 | 2.6 g |
| distilled water to | 100.0 g |

The procedure of Example 6 is followed. At first, the vaseline, paraffin oil, cholesterol, Miglyol ® and Span ® are melted together, then the water is added, and the active substance is suspended in the emulsion of the type water in oil.

EXAMPLE 8

| Hydrogel | |
| --- | --- |
| Zinc complex of 5-chloro-7-iodo-8-hydroxyquinoline | 6.0 g |
| Carbopol ® 934 (colloidal carboxyvinyl polymer, manufacturer: Biesterfeld | 0.9 g |
| triethanolamine | 1.0 g |
| methyl p-hydroxybenzoate | 0.1 g |
| isopropanol | 32.0 g |

| Hydrogel | |
|---|---|
| distilled water to | 100.0 g |

The methyl p-hydroxybenzoate is dissolved in a part of the distilled water. Carbopol(R) 934 is swollen in the solution obtained, then neutralized with the triethanolamine. After the addition of a suspension of the active substance in isopropanol, the volume is adjusted with distilled water to 100 g.

EXAMPLE 9

| Gel | |
|---|---|
| zinc complex of 5-chloro-7-iodo-8-hydroxyquinoline | 8.0 g |
| Carbowax 6000 [poly(ethylene glycol) monoalkyl ether, degree of polymerisation: 6000] | 15.0 g |
| Carbowax × 300 [poly(ethylene glycol) monoalkyl ether, degree of polymerisation: 300] | 30.0 g |
| Carbowax 400 [poly(ethylene glycol) monoalkyl ether, degree of polymerisation: 400] | 27.0 g |
| glycerol | 18.0 g |
| Brij³⁵ [poly(ethylene glycol) lauryl ether, degree of polymerisation: 23, manufacturer: Atlas] | 2.0 g |

The components, with the exception of the active substance, are melted together, the active substance is added to the melt in small portions under stirring, and the composition is homogenized.

EXAMPLE 10

| Vaginal suppository (pressed) | |
|---|---|
| zinc complex of 5-chloro-7-iodo-8-hydroxyquinoline | 0.4000 g |
| poly(ethylene glycol) (degree of polymerisation: 35,000) | 0.0087 g |
| talc | 0.0086 g |
| magnesium stearate | 0.0100 g |
| Aerosil R-200 (active silica, manufacturer: Degussa) | 0.0030 g |
| Mowilith DH, 100 percent(vinyl acetate polymer, manufacturer: Hoechst AG) | 0.0200 g |
| potatoe starch | 0.0240 g |
| ultra amylopectine | 0.0087 g |
| Avicel ® PH 101 (microcrystalline cellulose) | 0.0170 g |
| | 0.5000 g |

The components are homogenized in a fluidization apparatus under the following parameters:
inlet air temperature: 50° to 55° C.
outlet air temperature: 26° C.
pressure at the injector: 3 bar
flow rate of air; 3000 to 4000 m³/hr.
rate of addition: 800 ml/min.

water content of the granulate: 0.5 to 1.5 percent
disintegration time of the granulate: about 10 minutes.
The granulate is pressed to obtain vaginal suppositories.

EXAMPLE 11

| Vaginal suppository (moulded) | |
|---|---|
| zinc complex of 5-chloro-7-iodo-8-hydroxyquinoline | 0.4 g |
| Tween ® 61 (polyoxyethylene sorbitane monostearate, manufacturer: Atlas) | 0.6 g |
| Miglyol 812 | 0.8 g |
| Witepsol W 25 (artificial triglyceride of to coco and palm oil, manufacturer: Dynamit-Nobel) | 2.5 g |

Moulding is performed at a temperature of 38° to 41° C. under constant stirring.

EXAMPLE 12

| Dusting powder | |
|---|---|
| zinc complex of 5-chloro-7-iodo-8-hydroxyquinoline | 14.0 g |
| zinc stearate | 5.0 g |
| zinc oxide | 4.5 g |
| Aerosil ® R-200 | 3.8 g |
| talc to | 100.0 g |

The components are thoroughly homogenized to obtained a powder mixture.

EXAMPLE 13

| Suspension | |
|---|---|
| zinc complex of 5-chloro-7-iodo-8-hydroxyquinoline | 0.1 g |
| Brij ® 30 [poly(ethyleneglycol) lauryl ether, degree of polymerisation: 4, manufacturer: Atlas] | 1.7 g |
| sodium citrate | 2.5 g |
| methyl p-hydroxybenzoate | 0.1 g |
| Keltrol ® (polysaccharide prepared by fermentation) | 4.2 g |
| distilled water to | 100.0 g |

The methyl p-hydroxybenzoate is dissolved in a part of the distilled water, then Keltrol ® is swollen in the solution obtained. The sodium citrate and Brij ® 30 are dissolved in the remaining part of the distilled water. The active substance is added to the latter solution, then it is completed with the swollen Keltrol ®. The mixture is passed through a colloid mill to achieve the homogenization required.

Instead of Keltrol ®, the following substances can be used: alginic acid, sodium alginate, esters of alginic acid, poly(vinyl pyrrolidone), cellulosic derivatives, polymethacrylates or bentonite.

We claim:

1. A method of treating mycotic infections comprising administering to a patient having a mycotic infection a therapeutically effective amount of a zinc complex of 5-chloro-7-iodo-8-hydroxyquinoline of a formula (I)

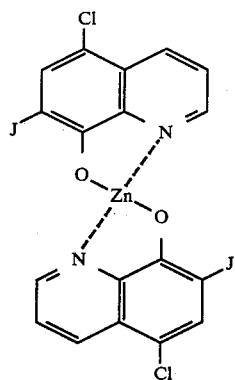
(I)

or a pharmaceutical composition thereof as an antimycotic agent.

2. The method of claim 1 wherein the antimycotic agent administered is a pharmaceutical composition.

3. The method of claim 2 wherein the pharmaceutical composition administered is in the form of a dusting powder, an ointment, a vaginal suppository, a gel, a hydrogel, a suspension or an emulsion.

4. The method of claim 3 wherein the pharmaceutical composition is in the form of an ointment.

5. The method of claim 4 wherein the ointment is a hydrophilic ointment.

6. The method of claim 4 wherein the ointment is a lipophilic ointment.

7. The method of claim 3 wherein the pharmaceutical composition is in the form of a vaginal suppository.

8. The method of claim 7 wherein the vaginal suppository is a pressed vaginal suppository.

9. The method of claim 7 wherein the vaginal suppository is a moulded vaginal suppository.

10. The method of claim 3 wherein the phamaceutical composition is in the form of a suspension or emulsion.

11. The method of claim 10 wherein the suspension or emulsion is administered in the form of an aerosol.

* * * * *

UNITED STATES PATENT AND TRADEMARK OFFICE
CERTIFICATE OF CORRECTION

PATENT NO. : 4,868,172
DATED     : September 19, 1989
INVENTOR(S) : Sebestyen et al.

It is certified that error appears in the above-identified patent and that said Letters Patent is hereby corrected as shown below:

On the title page:

[75] Inventors:   4th line, change "Egri János" to
                  --János Egri--

[73] Assignee:    Change "BASF Aktiengesellschaft
                          Ludwigshafen, Fed. Rep. of Germany"
                  to --EGIS Gyógyszergyár
                       30-38., Kereszturi ut,
                       Budapest X. - Hungary--

Signed and Sealed this

Twentieth Day of November, 1990

Attest:

HARRY F. MANBECK, JR.

*Attesting Officer*    *Commissioner of Patents and Trademarks*